United States Patent [19]
Volvovitz

[11] Patent Number: 5,976,552
[45] Date of Patent: *Nov. 2, 1999

[54] VIRUS VACCINES

[75] Inventor: Franklin Volvovitz, New Haven, Conn.

[73] Assignee: Protein Sciences Corporation, Meriden, Conn.

[*] Notice: This patent is subject to a terminal disclaimer.

[21] Appl. No.: 08/430,971

[22] Filed: Apr. 28, 1995

[51] Int. Cl.$^6$ .......................... A61K 39/145; C12N 15/63
[52] U.S. Cl. ..................... 424/199.1; 424/210.1; 435/69.3; 435/320.1
[58] Field of Search .............................. 424/210.1, 199.1; 435/69.3, 235.1, 320.1

[56] References Cited

PUBLICATIONS

Johansson et al. Dissociation of influenza virus hemagglutinin and neuraminidase eliminates their intravirionic antigenic competition. J. Virology vol. 67, pp. 5721–5723, 1993.
Johansson et al. Purified influenza virus hemagglutinin and neuraminidase are equivalent in stimulation of antibody response but induce contrasting types of immunity to infection. J. Virology vol. 63 pp. 1239–1246, 1989.
Kuroda et al. The oligosaccharides of influenza virus hemagglutinin expressed in insect cells by a baculovirus vector. Virology vol. 174, pp. 418–429, 1990.
Kuroda et al. Retarded processing of influenza virus hemagglutinin in insect cells. Virology vol. 180 pp. 159–165, 1991.
Chazenbalk et al. Expression of the extracellular domain of the thyrotropin receptor in the baculovirus system using a promiter active earlier than the polyhedrin promoter. J. Biol. Chem. vol. 270 pp. 1542–1548, 1995.
Physicians Desk Reference, 48th Edition, Medical Economics Data Production Co. pp. 1160–1162, 1994.
Ada, G.L., and Jones, P.D., Curr. Top. Microbiol. Immunol. 128: 1–54 (1986).
Kendal, A.P., et al., J. Infect. Dis. 136: S415–24 (1977).
Murphy, B.R., et al., N. Engl. J. Med. 286:1329–1332 (1972).
Nichol., K.L., et al., Arch. Int. Med. 152: 106–110 (1992).
Rocha et al. Comparison of 10 influenza A (H1N1) and H3N2) haemagglutinin sequences obtained directly from clinical specimens t those of MDCK cell–and egg–grown viruses. J. Gen. Virology vol. 74 pp. 2513–2518, 1993.
Nerome et al. Evolutionary pathways of N2 neuraminidases of swine and human influenza A viruses: origin of the neuraminidase genes of two reassortants (H1N2) isolated from pigs. J. Gen. Virology vol. 72 pp. 693–698 (1991).
Weyer et al. A baculovirus dual expression vector derived from the Autographa californica nuclear polyhedrosis virus polyhedrin and p10 promoters: co–expression of two influenza virus genes in insect cells. J. Gen. Virology vol. 72 pp. 2967–2974, 1991.
Vanlandschoot et al. Recombianant secreted haemagglutinin protects mice against a lethal challenge of influenza virus. Vaccine vol. 11 pp. 1185–1187, 1993.
Kilbourne Inactivated influenza vaccines. in Vaccines Plotkin and Mortimer, Eds., W.B. Saunders Co. Philadelphia pp. 420–434, 1988.

*Primary Examiner*—George C. Elliott
*Assistant Examiner*—John S. Brusca
*Attorney, Agent, or Firm*—Frommer Lawrence & Haug LLP; Thomas J. Kowalski

[57] ABSTRACT

Improved mammalian virus vaccines are combinations that contain an immunogenic amount of inactivated virus, such as influenza virus, Herpes varicella virus, measles virus, Epstein Barr virus, respiratory syncytial virus, parainfluenza 3, Herpes simplex type 1 virus, and Herpes simplex type 2 virus, and an immunogenic amount of a purified recombinant envelope protein from the virus, or a fragment or precursor of the protein. Alternatively, they contain either inactivated virus and/or envelope protein antigens and an adjuvant such as granulocyte-microphage colony stimulating factor. One embodiment of an influenza vaccine is prepared by combining inactivated virus, preferably three strains of the virus, and hemagglutinin, preferably a combination of respective hemagglutinins for each of the three strains present. In another embodiment, an influenza vaccine is prepared by combining inactivated virus, again preferably three strains of the virus, and neuraminidase, preferably a combination of respective neuraminidase for each of the three strains present. In a third embodiment, the vaccine contains inactivated virus and both hemagglutinin and neuraminidase, preferably using three strains of each. Granulocyte-macrophage colony stimulating factor is, optionally, added to these embodiments.

11 Claims, No Drawings

VIRUS VACCINES

TECHNICAL FIELD

This invention relates to improved virus vaccines for influenza, Herpesviruses, and the like.

BACKGROUND ART

Immunization to protect against communicable disease is one of the most successful and cost-effective practices of modern medicine. Smallpox has been completely eliminated by vaccination, and the incidence of many other dreaded diseases such as polio and diphtheria has been drastically reduced through immunization programs. However, vaccines, especially those based on the use of inactivated viruses, vary in effectiveness. For example, while the currently licensed influenza vaccine is reportedly over 80% efficacious in young adults, it is only approximately 60% efficacious in adults 65 years of age and older, and less than 50% effective in children under 2 years of age. The recently licensed chicken pox vaccine is reportedly approximately 70% efficacious, and there are currently no effective vaccines against many important viral diseases including those caused by respiratory syncytial virus, parainfluenza 3 virus, Rotavirus and the human immunodeficiency virus. In some cases licensed inactivated viral vaccines may cause adverse reactions which have prevented their use at the higher dosages needed to improve efficacy.

Inactivated virus vaccines confer protection by stimulating immune responses to proteins found in the free virus. Antibodies to the mature envelope proteins found on free virus may be optimal in blocking the initial events of infection (such as virus binding to a cell receptor and attachment and entry into a cell) following exposure to a virus, but may be sub-optimal once a virus has entered a cell. Once infected, the cells and the cell-associated immature virions contain precursors to the mature envelope proteins. These precursor proteins may stimulate more optimal immune responses for stemming the spread of infection and preventing clinical illness when the body's first line of defense, antibodies to free virus, does not completely prevent all virus from infecting cells.

Inactivated virus vaccines are typically produced from virus that has been grown in animal cells, e.g. embryonated eggs for influenza, which are then inactivated by treatment with chemicals such as formalin. Attenuated vaccines for measles and chickenpox are produced by growing weakened virus in cell cultures. Advances in the understanding of the pathogenesis of viral infections and recombinant DNA technology have led to the identification and production of specific viral proteins for use in subunit viral vaccines. These have been particularly successful in the formulation of a subunit vaccine against the hepatitis B virus.

Most existing licensed vaccines and vaccines in development, whether based on inactivated viruses or recombinant DNA technology, rely primarily on immune responses to the mature virus, or, in a few examples of experimental, recombinant DNA-based vaccines, immune responses to antigens found in the cell-associated form of the virus, or virus-infected cells. Both the killed virus and attenuated virus approaches on the one hand and the recombinant DNA approaches on the other hand have their advantages and their limitations. While the cell culture and embryonated egg methods are used to grow whole virus very inexpensively, they are not very efficient methods for the commercial production of the viral precursor proteins found in the infected cells and the cell-associated forms of the virus. This is because these methods act like miniature assembly lines and, while a large amount of mature virus accumulates in the cell cultures or the eggs at any given time, a much smaller amount of virus is actually in the process of being assembled. Therefore, the purified virus used to make the vaccine contains very little, if any, of the envelope precursor or other precursor proteins. On the other hand, viral membrane glycoproteins, in either their mature or precursor form, can be efficiently produced by recombinant DNA technology. When native conformational structure is needed to produce functional, neutralizing antibodies, the use of recombinant technology employing mammalian cell or insect cell substrates is preferred. However, production of viral vaccine proteins in insect or mammalian cells by recombinant methods is generally more expensive on a per milligram protein basis than cell culture and egg production methods.

Adverse reactions from vaccines may arise from impurities or from biologic properties of the vaccine proteins (antigens) responsible for conferring protective immunity. For example, the contaminating egg protein present in the licensed influenza vaccines may be largely responsible for the adverse reactions associated with these products. This source of adverse reactions can be reduced or eliminated in highly purified recombinant subunit protein vaccines.

Mature viral proteins present in vaccines may have biologic properties that are responsible for adverse reactions. Uptake by mononuclear cells and granulocytes of inactivated influenza virus mediated by the mature hemagglutinin may also be responsible for adverse reactions. The mature HIV envelope glycoprotein (gp120) in some experimental vaccines against HIV may bind to the CD4 receptor of T4 lymphocytes and alter normal immune function. It would be desirable to reduce potential adverse reactions through the use of the respective precursor proteins, e.g., HA0 in the case of influenza vaccines and gp160 in the case of HIV vaccines, in the vaccine preparations, or through other approaches.

The viral envelope proteins in inactivated virus vaccines are substantially glycosylated. While glycosylation is important in maintaining conformational structure of these proteins it may also reduce their immunogenicity. These proteins in either the mature of precursor form can be produced with trimmed carbohydrate residues with recombinant baculovirus expression vectors and insect cells. The baculovirus-produced proteins retain sufficient native conformation to stimulate functional neutralizing antibodies and may provide greater immunogenicity than highly glycosylated native proteins.

Infection by influenza virus causes substantial illness and premature death worldwide. Immunization with vaccines comprised of preparations of inactivated influenza viruses is currently the most useful practice for reducing disease from viral influenza. These inactivated vaccines have been licensed by regulatory bodies throughout the world. They confer protection against infection and disease by stimulating the production of immune responses to the hemagglutinin (HA), neuraminidase (NA), nucleoproteins (NP, M1) and possibly other proteins of component strains (Murphy, B. R., et al., *N. Engl. J. Med.* 268:1329–1332 (1972) and Kendal, A. P., et al., *J. Infect. Dis.* 136:S415–24 (1986)). The most important of these is the production of neutralizing antibodies to HA (Ada, G. L., and Jones, P. D., *Curr. Top. Microbiol. Immunol.* 128:1–54 (1986)). The currently available inactivated vaccines nevertheless have limitations, including sub-optimal immunogenicity and efficacy in adults 65 years of age and older and very young children and under utilization in part due to poor patient acceptance in connection with the belief that such vaccines are not very effective and fears of adverse reactions (Nichol, K. L., et al., Arch. Int. Med. 152:106–110 (1992)). The perception of lack of effectiveness arises in part from variations in potency from year to year and the association of many non-influenza respiratory tract illnesses with influenza.

The mature influenza virus contains both HA and NA proteins in its outer envelope. The HA is present as trimers. Each HA monomer consists of two polypeptides (HA1 and HA2) linked by a disulfide bond. These polypeptides are derived by cleavage of a single precursor protein, HA0, during maturation of the influenza virus. In part, because these molecules are tightly folded, the HA0 and the mature HA1 and HA2 differ slightly in their conformation and antigenic characteristics. Furthermore, the HA0 is more stable and resistant to denaturation and to proteolysis. Recently it has been reported that a baculovirus/insect cell culture derived recombinant HA0 conferred protective immunity to influenza (Wilkinson, B., MicroGeneSys Recombinanat Influenza Vaccine, PMA/CBER Viral Influenza Meeting, Dec. 8, 1994). One limitation of recombinant HA0 vaccines is their inability to stimulate immune responses against non-HA antigens which may provide greater and more durable protection, especially for high risk populations that do not respond well to immunization.

It would be desirable to provide improved virus vaccine preparations that do not exhibit as many of the limitations and drawbacks observed with the use of currently available vaccines.

SUMMARY OF THE INVENTION

It is an object of the invention to provide improved vaccines for virus infections such influenza, chicken pox, measles, respiratory syncytial virus, infectious mononucleosis, and Herpes simplex that have enhanced efficacy and safety over currently available vaccines.

It is another object of the invention to provide virus vaccines that provide greater and more durable protection, especially for high risk populations that do not respond well to immunization.

It is a further and more specific object of the invention to provide a vaccine designed to optimize immune responses observed with both free virus and cell-associated virus to provide better protection against infection and disease.

It is another specific object of the invention to provide an improved influenza vaccine.

These and other objects are accomplished by the present invention, which provides combination vaccines containing at least two components: inactive virus, recombinant envelope proteins from the same virus, and an adjuvant. Mammalian vaccine compositions of the invention typically comprise an immunogenic amount of inactivated virus such as influenza virus, Herpes varicella virus, measles virus, Epstein Barr virus, respiratory syncytial virus, parainfluenza 3 virus, Herpes simplex type 1 virus, and Herpes simplex type 2 virus and an immunogenic amount of a purified recombinant envelope protein from the virus, or a fragment or precursor of such a protein.

Preferred adjuvants are colony stimulating growth factors. Granulocyte-macrophage colony stimulating factor is particularly preferred in some embodiments.

Improved influenza virus vaccines typically contain inactivated virus and either recombinant hemagglutinin, recombinant neuraminidase, or mixtures thereof. In one embodiment, an improved influenza virus vaccine composition for human beings contains three inactivated strains of the virus and recombinant hemagglutinin from at least one, and preferably from each of the three strains. In another embodiment, an improved influenza vaccine contains three inactivated strains of the virus and recombinant neuraminidase from at least one, and preferably from each of the three strains. Some influenza vaccines embodiments contain both hemagglutinin and neuraminidase. In these embodiments, three strains of virus are preferably present, with at least two, and preferably two to six of the corresponding envelope proteins, or fragments or precursors thereof.

Other vaccine embodiments include inactivated Epstein Barr virus and recombinant virus gp340 envelope protein; inactivated respiratory syncytial virus and recombinant virus envelope F protein, G protein, and/or FG polyprotein; inactivated parainfluenza 3 virus and recombinant virus envelope F protein, HA protein, and/or F/HA polyprotein; inactivated measles virus and recombinant virus envelope F protein, HA protein and/or F/HA polyprotein; inactivated Herpes simplex type 1 virus and recombinant virus envelope glycoprotein D; and inactivated Herpes simplex type 2 virus and recombinant virus envelope glycoprotein D.

An improved chicken pox vaccine embodiment for human beings contains attenuated Herpes varicella and recombinant Herpes varicella envelope glycoprotein D.

Alternatively, granulocyte-macrophage colony stimulating factor is used as a vaccine component with either any of the above described envelope antigens or inactivated viruses, or both.

Methods for immunizing human beings against virus infections by inoculating with the combination vaccines, particularly by means of an intramuscular injection, are also disclosed.

DETAILED DESCRIPTION OF THE INVENTION

In the practice of the invention, vaccine preparations are combinations of at least two components: antigens derived from the free virus, antigens derived from precursor proteins of the cell associated virus, and adjuvants. The antigens are produced by a variety of methods including the use of virus infected cells (cell culture or embryonated eggs) or by recombinant DNA technology including live recombinant vector (vaccinia) or recombinant subunit protein (baculovirus/insect cells, mammalian cells, yeast, or bacteria).

Mammalian virus vaccine compositions of the invention comprise at least two components: an immunogenic amount of inactivated or attenuated virus, an effective amount of an adjuvant, and an immunogenic amount of a purified recombinant envelope protein, or a fragment or precursor thereof. Vaccines of the invention can be prepared against influenza virus, measles virus, chicken pox virus, Epstein Barr virus, respiratory syncytial virus, parainfluenza 3 virus, Herpes simplex type 1 virus, Herpes simplex type 2, and the like.

Viral envelope and envelope precursor proteins ("VEP") can be made recombinantly using any of the established expression systems, such as bacteria, yeast, baculovirus, and mammalian cell cultures. As used herein, the term "recombinant" refers to any protein or nucleic acid produced by any method employing well known nucleic acid manipulations, examples of which are provided below. As used herein, any protein or nucleic acid that results from, or is expressed from, a nucleic acid resulting from such manipulations is a recombinantly produced protein or nucleic acid.

The DNA used to produce VEP may be genomic DNA, in which case it may include introns, or it may be cDNA which is prepared in vitro from mRNA using a reverse transcriptase and which contains open reading frames. Methods for isolation, cloning or synthesizing DNA and cDNA are well known to those of skill in the art. Expression refers to the process by which nucleic acid is transcribed and translated into peptides, polypeptides, or proteins. If the nucleic acid is derived from genomic DNA, expression may, if an appropriate eukaryotic host cell or organism is selected, include splicing of the mRNA and subsequent glycosylation. An expression vector refers to a recombinant DNA or RNA construct, such as a plasmid, a phage, recombinant virus or other vector that, upon introduction into appropriate host cells, causes nucleic acid molecules that have been cloned into the vector to be transcribed, and then translation of the transcribed nucleic acid into a polypeptide. The nucleic acid molecule is cloned into the vector in such a manner that it is operably linked to regulatory sequences that effect expression of the heterologous nucleic acid molecules. Upon expression in a selected host cell or organism, if the appropriate regulatory sequences are operably linked to the DNA or included in the heterologous DNA, the expression product may be exported to the cytoplasm and/or may be secreted out of the host cell.

Appropriate expression vectors are well-known to those of skill in the art and include those that are replicable in eukaryotic cells and/or prokaryotic cells. Such expression vectors may remain episomal or may integrate into the host cell genome.

In all cases, the VEP cDNA or gene can be inserted into appropriate expression vectors containing expression regulatory elements, such as transcription initiation signals, translation initiation signals, starting codon, termination codon, transcription terminating signals, polyadenylation signals, and others. Suitable vectors are commercially available from a variety of companies. After the recombinant vectors containing VEP-encoding DNA are transfected into the host cells, they may remain as extrachromosomal DNA or they may be integrated into the host genome. In either case, they may direct the synthesis of recombinant VEP in the host cells. Some examples for the expression of heterologous genes are described in *Methods in Enzymology*, Vol. 153, Chapters 23 to 34 (Wu and Grossman, eds., Academic Press, 1987). Large scale culture of the VEP synthesizing host cells and the purification of the protein may form a cost effective commercial means of production of VEP. Methods are well known to those skilled in the art for the large scale production of proteins. Many methods and reagents useful for recombinant expression of VEP are described in *The 1995 Lab Manual Source Book* (Cold Spring Harbor Laboratory Press, N.Y., 1995).

Some examples of potentially useful expression systems for VEP include, but are not limited to, those using *E. coli* or other bacteria as host. Many mammalian cDNA's have been expressed in *E. coli* and many expression vectors with different promoters, operators, and other regulatory elements are available commercially. A typical vector construction and expression is described by Lin and Tang, *J. Biol. Chem*. 264: 4482–4489 (1989). The expression of some eukaryotic proteins in the cytosol of *E. coli* produces insoluble 'inclusion bodies' and would require the refolding of recombinant protein. However, the use of a 'leader' sequence, such as omp, described by Duffaud, et al., in *Methods in Enzymology* 153: 492–506 (Wu and Grossman, eds., Academic Press, 1987), will direct the proper folding and also export of the recombinant VEP to the periplasmic space of the bacteria.

Alternatively, yeast may be employed as a host. The principles for the expression of recombinant VEP in the yeast are similar to those for *E. coli* expression. Examples are provided by Bitter, et al., in *Methods in Enzymology* 153: 516–544 (Wu and Grossman, eds., Academic Press, 1987). Like *E. coli*, yeast host cells may express a foreign gene either in the cytosol or as secreted protein. Unlike *E. coli* expression, the secreted expression in yeast is capable of glycosylation.

Fungi may also be used as a host. There are small numbers of fungal expression vectors which have been successfully used to express heterologous genes. The existing fungal expression vectors integrate themselves into the host genome after transfection as indicated by Cullen et al., in *A Survey of Molecular Cloning Vectors and their Uses*, (Butterworth Publishers, Stoneham, Mass. 1986). When a leader is present in front of the expressed protein codons, the secreted recombinant proteins can be glycosylated. Some examples of successful expressions involve bovine chymosin, described by Cullen et al., *Bio/Technology* 5: 369–378 (1987), and an acid protease from a different fungus, described by Gray, et al., *Gene* 8: 41–53 (1987).

Insect cells can be used as hosts, and are preferred in some embodiments. Baculovirus expression vectors for the synthesis of foreign genes in insect cells have been successfully used to express many eukaryotic and viral proteins. This system is capable of glycosylation and can also express recombinant proteins at a high level. The use of this system has been reviewed in some detail by Luckow and Summers, *Bio/Technology*, Sep. 11, 1987 and by Luckow in the *Laboratory Manual for Baculovirus Expression Systems*, 1994). The recombinant VEP can also be expressed in insect cells using other expression vectors such as Entomopox viruses and cytoplasmic polyhedrosis viruses (CPV).

Finally, mammalian cells can serve as hosts. Many heterologous genes have been expressed in mammalian cells on a commercial scale. The commercial production of recombinant human tissue plasminogen activator is an example. Most of these expression vectors contain 1) either a mammalian promoter, such as metallocyanin or growth hormone, or viral promoters, such as SV40 early promoter or long terminal repeats of viral genes; 2) polyadenylation signals; and 3) appropriate regulatory elements for *E. coli* cloning including antibiotic resistance genes. After the insertion of the VEP gene downstream from the promoter, the vector can be first cloned in *E. coli*, isolated and transfected into mammalian cells. Neomycin or similar resistant selection markers can be either cotransfected in another vector or in the same vector. For high level expression, a gene amplification system is advantageous. For example, the expression vector can contain the gene of dihydrofolate reductase (dhfr). When the dhfr-strain of Chinese hamster ovary (CHO) cells are used, the cloned gene can be coamplified with that of dhfr by adapting the transformed cells to increasing methotrexate concentration. The transformant clones secreting VEP can be identified by enzyme assays or by western blots. Successful examples of this approach include the synthesis of recombinant prorenin, described by Poorman et al., *Proteins* 1: 139–145 (1986), and human immune interferon, described by Scahill et al., *Proc. Natl. Acad. Sci., U.S.A*. 80: 4654–4658 (1983).

Methods for purifying recombinant VEP are well known and can be generally divided into chromatographic methods, for example, ion exchange chromatography, molecular weight sieving, high pressure liquid chromatography, affinity chromatography, and electrophoretic methods, e.g., electrophoresis on agarose or acrylamide gels and isoelectric focusing. Any of these methods can be adapted to purify VEP.

A preferred method of purification is affinity chromatography. In immunoaffinity chromatography, an antibody to VEP is immobilized on a chromatographic substrate, a mixture containing VEP is applied to the substrate under conditions allowing the antibody to bind VEP, the unbound material is removed by washing, and the bound VEP is eluted using, for example, high or low pH, protein denaturants or chaotropes.

For example, VEP may be purified by affinity chromatography using one or a combination of immobilized antibodies such as those described below covalently bound to agarose beads or bound non-covalently via a goat-anti mouse IgM antibody to *Staphylococcus aureaus* protein G beads. VEP isolation can also be achieved, for example, by incubating cell extracts with anti-VEP antibodies, described below, attached to a solid phase, such as chemical conjugation to agarose beads. After incubation, the beads are washed, denatured and resolved on a polyacrylamide gel.

To prepare vaccines, VEP or immunogenic fragments of VEP are combined with the respective inactivated virus from which the VEP is originally derived as described above. The combined inactivated virus and VEP preparation can be formulated and packaged using methods and materials known to those skilled in the art of vaccines, examples of which are described below. As used herein, an immunogenic fragment of a protein is a protein fragment of at least five to eight amino acids that elicits an immune response in an animal or individual.

Adjuvants may, optionally, be employed and are preferred in some embodiments. The above-described combination vaccines can be combined with an adjuvant, in an amount effective to enhance the immunogenic response. A common adjuvant widely used in humans is alum, that is, aluminum phosphate or aluminum hydroxide. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, and phospholipid conjugates such as those described by Goodman-Snitkoff, et al., J. Immunol. 147: 410–415 (1991), and incorporated by reference herein, can also be used.

For oral administration, it is known that an admixture of trace amounts of cholera toxin (CT), either cholera toxin subunit A, cholera toxin subunit B, or both, and a second antigen stimulate a mucosal immunity to the co-administered antigen. Furthermore, there is a dramatic humoral immune response to the second antigen instead of the immune tolerance that is elicited by oral delivery of the antigen alone. Thus, mucosally delivered CT functions as a powerful immunostimulant or adjuvant of both mucosal and humoral immunity. It is therefore preferred to enhance immunogenicity of the orally administered antigen by including CT in the vaccine.

For parenteral administration, adjuvants include muramyl dipeptides, muramyl tripeptide, cytokines, diphtheria toxoid, and exotoxin A. Commercially available adjuvants include QS-21® from Cambridge Biosciences, Worcester, Mass., and monophosphoryl lipid A (MPLA) from Ribi Immunochem.

A group of growth factors termed colony stimulating factors which support survival, clonal expansion, and differentiation of hematopoietic progenitor cells are also useful as adjuvants. Granulocyte-macrophage colony stimulating factor (GM-CSF) belongs to this group and induces partially committed progenitor cells to divide and differentiate in the granulocyte-macrophage pathways. GM-CSF is also capable of activating mature granulocytes and macrophages. The various cellular responses (i.e., division, maturation, activation) are induced through GM-CSF binding to specific receptors expressed on the cell surface of target cells. A recombinant form of GM-CSF is commercially available from the Immunex Corporation, Seattle, Wash. and sold under the name LEUKINE®. LEUKINE® is a glycoprotein of 127 amino acids characterized by 3 primary molecular species having molecular masses of 19,500,16,800 and 15,500 daltons. The amino acid sequence of LEUKINE differs from the natural human GM-CSF by a substitution of leucine at position 23, and the carbohydrate moiety may be different from the native protein (LEUKINE Product Insert, Immunex Corporation, 1992).

GM-CSF has been traditionally used to accelerate myeloid recovery in patients with non-Hodgkin's lymphoma (NHL), acute lymphoblastic leukemia (ALL) and Hodgkin's disease undergoing autologous bone marrow transplantation (BMT). After autologous BMT in patients with NHL, ALL or Hodgkin's disease, GM-CSF has been found to be safe and effective in accelerating myeloid engraftment, decreasing median duration of antibiotic administration, reducing the median duration of infectious episodes and shortening the median duration of hospitalization. It has recently been discovered that when GM-CSF was given to cancer patients together with recombinant carcinoembryonic antigen (rCEA) the immune response to rCEA was substantially greater than when patients received rCEA alone. It has been previously reported in the scientific literature that tumor cells can be transformed to express GM-CSF. In laboratory animals, immune responses to these transformed cells were greater than to non-GM-CSF transformed cells.

The commercially available GM-CSF from the Immunex Corporation is provided as a sterile, white, preservative-free, lyophilized powder and is intended for intravenous infusion following reconstitution with 1 ml sterile water for injection, USP. The pH of the reconstituted, isotonic solution is 7.4±0.3. The specific activity of LEUKINE® is approximately $5\times10^7$ colony-forming units per mg in a normal human bone marrow colony assay. When used as an adjuvant LEUKINE may be reconstituted with sterile water or with the vaccine preparation. If reconstituted with water then LEUKINE is administered by intramuscular injection at the same site as immunization with the vaccine or is first mixed with the vaccine preparation. The vaccine/GM-CSF mixture obtained by either reconstituting the GM-CSF with the vaccine preparation directly or by mixing the water reconstituted GM-CSF with the vaccine is then administered by intramuscular, subcutaneous or intradermal injection. Each single-use vial of LEUKINE contains either 250 μg or 500 μg of yeast-derived recombinant human GM-CSF.

In each of the prior examples of combination viral vaccines the final vaccine formulation is further modified by addition of an effective amount of GM-CSF to increase immunogenicity. This is accomplished by reconstituting the 500 μg GM-CSF vial with 1 ml of the described combination vaccine preparation. Alternatively, the 500 μg vial of GM-CSF can be reconstituted with 1 ml of sterile water and 0.5 ml of the reconstituted GM-CSF mixed with 0.5 ml of the combination vaccine preparation.

GM-CSF is also useful as an adjuvant for inactivated viral vaccines and attenuated viral vaccines without the addition of VEP. An effective amount of GM-CSF can be added as described above to the commercially available inactivated vaccines for viral influenza to improve immunogenicity. This is particularly important in young children and adults 65 years of age and older. An effective amount of GM-CSF can be added to the commercially available vaccine for herpes varicella to improve efficacy. This is particularly important in children afflicted with leukemia in whom this infection can be fatal. This is accomplished by reconstituting the 500 μg GM-CSF vial with 1 ml of the commercial influenza vaccine or 1 ml of the commercial herpes varicella vaccine. Alternatively, the 500 μg vial of GM-CSF can be reconstituted with 1 ml of sterile water and 0.5 ml of the reconstituted GM-CSF mixed with 0.5 ml of the commercial influenza vaccine or 0.5 ml of the commercial herpes varicella vaccine.

GM-CSF is also useful as an adjuvant with the licensed hepatitis B vaccines including both recombinant and non-recombinant forms. This is particularly important in adults 50 years of age and older, because of the lower efficacy rates of the licensed hepatitis B vaccines in older adults. GM-CSF adjuvanted hepatitis B vaccines can also be used therapeutically for individuals infected with hepatitis B virus.

GM-CSF is also useful as an adjuvant with recombinant viral membrane proteins such as influenza HA0 antigens. In this example an effective amount of recombinant HA0 described in following examples is added to GM-CSF either by direct reconstitution or by mixing with water reconstituted GM-CSF as described above. For the broader population, a vaccine containing 10 μg of each HA0 and 100 μg GM-CSF provides improved protection. For young children and adults 65 years and older a vaccine containing 50 μg of each HA0 and 250 μg GM-CSF provides improved protection.

GM-CSF is also useful as an adjuvant with recombinant VEP from a broad variety of viruses to produce vaccines where none are commercially available today. These include the use of an effective amount of GM-CSF in combination with an effective amount of HIV gp160 and/or gp120 protein for an AIDS vaccine, an effective amount of GM-CSF in combination with an effective amount of respiratory syncytial virus F protein and/or G protein, an effective amount of GM-CSF in combination with an effective amount of parainfluenza 3 virus F protein and/or HA protein, an effective amount of GM-CSF in combination with an effective amount of measles virus F and/or HA protein, and an effective amount of GM-CSF in combination with the glycoprotein D of Herpes viruses. In the case of Herpes viruses the GM-CSF adjuvant is useful in both prophylactic and therapeutic vaccines.

GM-CSF adjuvant is also useful in combination with self antigens. The alpha subunit of human chorionic gonadatropin (HCG) has been extensively tested as a potential contraceptive vaccine by itself and in various formulations including conjugation with Diphtheria toxoid and microencapsulation with the adjuvant MDP. However, greater immunogenicity in humans is needed. This is accomplished through the use of an effective amount of GM-CSF in combination with an effective amount of the alpha subunit of HCG conjugated to a Diphtheria toxoid carrier or an effective amount of a polyprotein containing the alpha subunit of HCG and diphtheria toxoid. Other self antigens that have been studied as contraceptive vaccines are the sperm HP-20 and HP-30 molecules. High levels of antibodies are needed for this approach to be effective. This is accomplished through the use of an effective amount of GM-CSF in combination with an effective amount of the HP-20 or HP-30 proteins.

GM-CSF is generally useful to improve the effectiveness and reliability of numerous vaccines including commercially available polysaccharide and conjugated polysaccharide vaccines for *Hemophilis influenza*. This is particularly important in children under 2 years of age who do not respond reliably to the commercially available vaccines.

GM-CSF is also useful to improve the immune response to antigens derived from infectious agents that cause chronic parasitic diseases including malaria, syphilis, hookworm, schistosomiasis. Because these organisms must remain in the host for extended periods of time they have evolved in ways that reduce their immunogenicity to the host organism. For example a recombinant *Plasmodium falciparum* cirumsporozooite antigen that was highly immunogenic in laboratory animals was not immunogenic in humans. An effective amount of GM-CSFin combination with an effective amount of *Plasmodium falciparum* cirumsporozooite antigen improves immunogenicity in humans.

In the foregoing examples a preferred amount of GM-CSF is 500 μg of GM-CSF obtained from a 500 μg single-dose vial of LEUKINE that is commercially available from the Immunex Corporation. Unless otherwise stated in the foregoing examples a preferred amount of antigen is 100 μg for each antigen included in the vaccine preparation.

Numerous carriers for administration of vaccine compounds are known. These include, but are not limited to, simple liquid carriers, and polymeric and lipid compositions. Simple liquid carriers, such as water or a buffered saline, can be used, either alone or in combination with other carriers.

The carrier may also be a polymeric delayed-release system. Synthetic polymers are particularly useful in the formulation of a vaccine to effect the controlled release of antigens. An example of this is described by Kreuter, *Microcapsules and Nanoparticles in Medicine and Pharmacology*, pages 125–148 (M. Donbrow, ed., CRC Press). The use of other particles have demonstrated that the adjuvant effect of these polymers depends on particle size and hydrophobicity.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters, and polyamides, particularly those that are biodegradable.

A frequent choice of a carrier for pharmaceuticals and more recently for antigens is poly (d,1-lactide-co-glyco-lide) (PLGA). This is a biodegradable polyester that has a long history of medical use in erodible sutures, bone plates and other temporary prostheses, where it has exhibited no toxicity. A wide variety of pharmaceuticals including peptides and antigens have been formulated into PLGA microcapsules. A body of data has accumulated on the adaptation of PLGA for the controlled release of antigen, for example, as reviewed by Eldridge et al., *Current Topics in Microbiology and Immunology* 146: 59–66 (1989). The PLGA microencapsulation process uses a phase separation of a water-in-oil emulsion. In this process, the inactivated virus and the respective VEP of the combination vaccine are prepared as an aqueous solution and the PLGA is dissolved in a suitable organic solvent such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Proteosomes, combinations of protein and liposomes, can also be used as carriers for combination vaccines, using the inactivated virus and the respective VEP of the combination vaccines as the protein component. The procedures and materials for the use of proteosomes are as described in Lowell et al., Science 240: 800 (1988); Lowell, in *New Generation Vaccines* (Woodrow and Levine, eds., Marcel Dekker, N.Y., 1990), Ch. 12, pages 141–160; and Orr et al., *Infect. Immun.* 61: 2390 (1993), the teachings of which are incorporated herein.

It will be understood by those skilled in the art that the immunogenic vaccine composition can contain other physiologically acceptable ingredients such as water, saline or a mineral oil such as Drakeol™, Markol™, and squalene, to form an emulsion, or in combination with aqueous buffers, or encapsulated within a capsule or enteric coating to protect the protein from degradation while passing through the stomach.

In a preferred embodiment, the vaccine is packaged in a single dosage for immunization by parenteral, that is, intramuscular, intradermal or subcutaneous, administration; or nasopharyngeal, that is, intranasal, administration. The effective dosage is determined using standard techniques, such as antibody titer. The antigen may be lyophilized for resuspension at the time of administration or in solution. If administered with adjuvant, the adjuvant may be administered in combination with or in the vicinity of the vaccine.

Immunity is measured using assays to detect and quantitate antibodies that bind to the VEP. Cellular immunity is measured using assays that measure specific T-cell responses such as delayed type hypersensitivity (DTH) and lymphocyte proliferation. The dosage is determined by the antigen loading and by standard techniques for determining dosage and schedules for administration for each antigen, based on titer of antibody elicited by the antigen administration. As used herein, a dose effective to elicit an immune response is considered to be one that causes antibody titer to increase compared to untreated animals or individuals, using any of the known methods of titering antibodies.

Circulating antibodies to recombinant VEP are detected by enzyme immunoassay using recombinant VEP as antigen. Such assays are described below. Briefly, plates can be coated with 1 microgram of recombinant VEP per well. Horse radish peroxidase (HRP)-conjugated goat anti-dog IgG antibodies is used at 1:1,000 dilution. Immune responses can also be measured by immunofluorescence (IFA), two-direction agarose diffusion and by Western/immunoblotting as described by Liu Shu-xian et al., *SE Asian J. Trop. Med. Pub. Health* 24: 61–65 (1993).

Improved influenza vaccines are prepared in one embodiment. An immunogenic amount of inactivated influenza virus is combined with an immunogenic amount of a recombinant influenza virus envelope protein, or a fragment or a precursor of an envelope protein. By "immunogenic" is meant capable of eliciting an immune response.

Any influenza envelope protein, or protein fragment or precursor, may be employed. Hemagglutinin, neuraminidase, or mixtures of hemagglutinin and neuraminidase are employed in preferred embodiments. The recombinant proteins are prepared using standard means such as production using baculovirus vectors in insect cell cultures, such as lepidopteran cell cultures as described by Powers, D. C., et al., (1995). Alternatively, the proteins can be prepared using mammalian expression systems such those using COS cells or CHO cell expression vectors as described by Ausubel, F. M., et al., *Short Protocols in Molecular Biology*, 2nd ed., John Wiley, New York, 1992, pp. 16–53 to 16–62. The baculovirus/lepidopteran method is employed in one embodiment.

For influenza, the preferred combination vaccine contains inactivated influenza virus for three strains of virus in a given epidemic season such as those commercially available and illustrated in the Examples hereinafter. Strains selected by FDA and CDC for representative epidemic seasons are shown in the following table.

| Strain | 1992/93 | 1993/94 | 1994/95 |
| --- | --- | --- | --- |
| H1N1 | A/Texas/36/91 | A/Texas/36/91 | A/Texas/36/91 |
| H3N2 | A/Beijing/353/89 | A/Beijing/32/92 | A/Shangdong/9/93 |
| B | B/Panama/45/90 | B/Panama/45/90 | B/Panama/45/90 |

The licensed vaccine against the H1N1, H3N2 and B strains selected by FDA and CDC for the epidemic season is preferred in the practice of the invention. In these embodiments, an immunogenic amount of at least one of the respective recombinant envelope proteins such as HA0 or NA is employed in the combination vaccine, preferably one protein (or fragment or precursor) for each of the selected strains. Where protein fragments or precursors are employed in the recombinant protein component, the vaccines may contain a mixture of proteins and fragments or precursors.

In alternative embodiments, the combination vaccine contains two envelope proteins such as hemagglutinin and neuramlinidase. Where the vaccine contains three strains, the combination vaccine contains at least one hemagglutinin and at least one neuraminidase. Preferred embodiments contain a hemagglutinin corresponding to each strain and a neuroaminidase for each strain.

The amount of inactivated virus present in the combination vaccine for each strain is typically adjusted so that the vaccine contains from about 12 to about 18 $\mu$g viral envelope protein for each strain; in one embodiment, the amount of inactivated virus is adjusted such that the vaccine contains 15 $\mu$g of viral HA (HA1 +HA2) for each strain per dose. In one embodiment, about 15 $\mu$g of recombinant HA0 for each of the respective strains is employed.

Although monomeric HA0 or other polymeric forms may be present and monomeric or other forms of NA may be present, the preferred HA0 used is primarily in the form of trimers and NA in the form of tetramers, with either or both produced with recombinant baculovirus vectors in lepidopteran cell cultures and extracted and purified under non-denaturing conditions to at least 90% purity.

An advantage of the invention is that the combination inactivated/recombinant influenza vaccine is less costly, safer and more effective than either product on its own and could receive licensure faster than the recombinant HA0 vaccine by itself. The combination vaccine would be optimized to stimulate immunity to antigens in the free virus (e.g., HA1, HA2) and to antigens of cell associated virus and virus infected cells (e.g., HA0), and further optimized to stimulate immunity by including natively glycosylated (inactivated influenza virus) and trimmed glycosylated (baculovirus/insect cell derived HA0) antigens.

Another advantage of the invention is that, by manipulation of the inactivated virus component and the envelope protein component, improved vaccines for influenza can be provided in several dosage levels required for healthy adults, and in high dosage levels for older adults and young children.

This invention encompasses other virus vaccines against such diseases as chicken pox, measles, respiratory syncytial virus, infectious mononucleosis, and Herpes simplex. A virus vaccine for chicken pox, for example, is prepared by combining attenuated Herpes varicella with recombinant protein Herpes varicella envelope glycoprotein D (or fragment or precursor). The preparation of a chicken pox vaccine is illustrated hereafter.

A measles vaccine is prepared by combining inactivated measles virus and recombinant measles virus envelope F protein, virus envelope HA protein, virus envelope F/HA polyprotein, or mixtures of these envelope proteins (or fragments or precursors).

Other vaccines of the invention include, but are not limited to a combination of inactivated Epstein Barr virus and recombinant virus gp340 envelope protein (or fragment or precursor); a combination of inactivated respiratory syncytial virus and virus envelope F protein, virus envelope G protein, virus envelope FG polyprotein, or mixtures of any of these proteins (or fragments or precursors); a combination of inactivated parainfluenza 3 virus and virus envelope HA protein, virus envelope HA protein, virus envelope F/HA polyprotein, or mixtures of any of these proteins (or fragments or precursors); a combination of inactivated Herpes simplex type 1 virus and recombinant virus envelope glycoprotein D (or fragment or precursor); and inactivated Herpes simplex type 2 virus and recombinant virus envelope glycoprotein D (or fragment or precursor).

In the case of improved influenza vaccines, it is an advantage of the invention is that FDA licensure requirements for the combination vaccine may be met by simple equivalency testing rather than full-scale phase III field trials. Testing in high-risk groups, where improved efficacy is expected in very young and elderly individuals, would be simplified because licensed vaccine components are contained in the combination vaccine. Scale-up and manufacturing demands would not be as great because less antigen is needed than would be necessary for a stand-alone recombinant protein vaccine such as the HA0 vaccine. It is also an advantage of the invention that incorporation of an adjuvant such as granulocyte-macrophage colony stimulating factor markedly increases the efficacy of the vaccines.

EXAMPLES

The following examples are presented to further explain and illustrate the invention and are not to be taken as limiting in any regard. Unless otherwise indicated, all parts and percentages are by weight and are given based on the weight of the composition at the indicated stage of processing.

EXAMPLE 1

This example illustrates formulations for combination influenza vaccines of the invention that employ any one of three commercially available inactivated influenza vaccines obtained and isolated from chicken embryos using standard means.

The three influenza vaccines are Fluzone® from Connaught Laboratories (Swiftwater, Pa.), Fluagen® from Parke Davis (Morris Plains, N.J.) and Flushield® from Wyeth Ayerst Laboratories (Philadelphia, Pa.). Descriptions of these products including dosage, prescribing information, adverse reactions, method of administration and production methods are published in the *Physicians Desk Reference*, 49th edition, Medical Economics Data Production Company, Montvale, N.J., 1995 (pages 908, 2660, 2740), and in the product insert accompanying the commercial product. (Additional product information is also available from the Food and Drug Administration under the Freedom of Information Act including the Summary Basis for Approval for each licensed influenza vaccine.)

Combination inactivated virus/recombinant HA0 influenza vaccines are prepared from a standard adult dose of any one of the the above mentioned licensed influenza vaccines by addition of 0.5 ml HA0 trivalent antigen in phosphate buffered saline solution at pH 7, prepared as described by Powers, D. C., et al.,(1995). Briefly stated, the recombinant HA0 are produced in cultures of Lepidopteran cells following infection with a baculovirus vector containing a cDNA insert encoding the HA gene. The expressed protein is purified under non-denaturing conditions to >95%, as measured by quantitative scanning densitometry of the bulk antigen electrophoresed on sodium dodecyl sulfate-polyacrylamide gels. The identity of the peptide is confirmed by amino acid analysis, N-terminal sequencing and Western blot analysis with anti-influenza sera. It is preferred that the HA0 antigen be in the form of trimers (although monomeric HA0 or other oligomeric forms may be used).

The HA0 trivalent antigen contains the respective HA0 for each of the three influenza strains present in the commercial vaccine being used to make the combination vaccine for a given epidemic season: A/Beijing/353/89, A/Texas/36/91, and B/Panama/45/90; A/Beijing/32/92, A/Texas/36/91, and B/Panama/45/90; or A/Shandong/9/93, A/Texas/36/91, and B/Panama/45/90. Each HA0 is adjusted to a final concentration of 30 $\mu$g per ml in the antigen preparation, so that, following addition of the trivalent antigen to the inactivated virus vaccine, the combination vaccine contains 15 $\mu$g of each recombinant HA0.

The combination vaccine is administered as a single 1 ml dose injected into the deltoid muscle. It is most efficacious if the injection is given in the fall preceding the influenza epidemic outbreak.

EXAMPLE 2

A combination vaccine for Herpes varicella (chicken pox) is prepared in this example.

An attenuated chicken pox (Herpes varicella) vaccine manufactured by Merck and Co. (West Point, Pa.) recently licensed by the Food and Drug Administration and reported to be 70% efficacious is employed in the formulation. Descriptions of this product including dosage, prescribing information, adverse reactions, method of administration, production methods, are published in the insert accompanying the commercial product. (Additional product information is also available from the Food and Drug Administration under the Freedom of Information Act including the Summary Basis for Approval for this vaccine.)

A combination attenuated virus/recombinant envelope protein Herpes varicella vaccine is prepared from a standard dose of the above-referenced licensed chicken pox vaccine by addition of 0.5 ml recombinant Herpes varicella antigen in phosphate buffered saline solution, pH 7. This antigen contains recombinant Herpes varicella envelope glycoprotein D protein at a concentration of 100 $\mu$g per ml.

The glycoprotein D antigens are produced as the respective precursor proteins with recombinant baculovirus vectors in lepidopteran cell cultures and extracted from purified cell membranes and purified under non-denaturing conditions to at least 90% purity. It is preferred that the envelope glycoprotein D antigens present in the Herpes varicella antigen so obtained are in the form of tetramers (although monomeric, dimeric or other oligomeric forms may also be used).

The preferred dosage of the combination vaccine is a single 1 ml dose administered by intramuscular injection in the deltoid muscle. A 1 ml booster dose may be advantages ministered one month following the initial immunization.

EXAMPLE 3

This example illustrates the preparation of several other combination vaccines of the invention, including a measles combination vaccine, an Epstein Barr virus combination vaccine, a respiratory syncytial virus combination vaccine, a parainfluenza 3 virus combination vaccine, a Herpes simplex type 1 combination vaccine, and a Herpes simplex type 2 combination vaccine. Highly purified recombinant viral envelope proteins (mature or precursor forms) in combination with the respective inactivated virus vaccines are combined to make the vaccines.

An attenuated measles virus vaccine commercially available from Merck and Co. is used for the measles combination vaccine. Inactivated preparations of the other viruses are prepared as heretofore described [citations?]. In general, each of these viruses are readily grown in mammalian cell cultures. The virus is harvested and concentrated by tangential flow filtration. Virus is further purified by centrifugation or column chromatographic methods based on size exclusion or lectin affinity. The purified virus is inactivated by a variety of methods, preferably by use of photo inactivation following treatment with psoralin to cross-link viral DNA so that the outer envelope proteins are not denatured.

The viral envelope proteins responsible for cell binding and cell fusion for each of the above-mentioned viruses and their respective precursor proteins have been described. The production of these proteins by one or more recombinant methods including baculovirus/insect cell culture and mammalian expression systems has also been described [citations or a review?]. A preferred method of recovering these proteins is to first purify the cell membranes containing the recombinant protein and then extract the protein from the membranes under non-denaturing conditions. The purified proteins typically form higher ordered structures as they do when present in the virus (dimers, trimers or tetramers). It is preferred that these oligomeric forms be used in the combination vaccine although the monomeric form are useful. Recombinant antigens are at least about 90% pure (although antigen of lesser or greater purity may also be used).

Preferred recombinant envelope antigens for the viruses other are as follows:

| Virus | Envelope Antigen |
|---|---|
| Epstein Barr virus | gp340 |
| Respiratory Syncytial virus | F protein, G protein, FG polyprotein |
| Parainfluenza 3 | F protein, HA protein, F/HA polyprotein |
| Measles virus | F protein, HA protein, F/HA polyprotein |
| Herpes varicella virus | envelope glycoprotein D |
| Herpes simplex type 1 | envelope glycoprotein D |
| Herpes simplex type 2 | envelope glycoprotein D |

The recombinant antigen contained in phosphate buffered saline, pH 7, is mixed with the respective inactivated virus, also in phosphate buffered saline, pH 7. The amount of antigen and the amount of inactivated virus present in the combination vaccine is adjusted such that 1 ml of the vaccine contains 50 μg of each envelope protein present in the antigen preparation, and an amount of virus calculated to contain 50 μg of the mature envelope protein responsible for binding to the cell receptor.

The preferred dosage of each combination vaccine is a single 1 ml dose administered by intramuscular injection in the deltoid muscle followed one month later by a single 1 ml booster dose administered by intramuscular injection in the deltoid muscle.

EXAMPLE 4

This example describes a high dose influenza combination vaccine. For adults 65 years of age and older and children under the age of 2 a preferred formulation for the combination inactivated virus/recombinant HA0 influenza vaccines described in Example 1 contains 150 μg of each recombinant HA0 or 100 μg of each recombinant HA0 instead of the 15 μg amount described in Example 1.

Each HA0 is adjusted to a final concentration of 300 μg per ml or 200 μg per ml in the antigen preparation, so that, following addition of the trivalent antigen to the inactivated virus vaccine, the combination vaccine contains 150 μg of each recombinant HA0 or 100 μg of each recombinant HA0.

To achieve concentrations of recombinant HA0 at a concentration of 200 μg or greater, the eluate from the final column step is further concentrated by repeating this step, but reducing the column size and packed resin bed by 50% to 75% and proportionately reducing the volume of elution buffer. Alternatively, each recombinant HA0 is concentrated by pressure dialysis in a stirred cell.

The preferred dosage of the high dose combination vaccine is a single 1 ml dose administered by intramuscular injection in the deltoid muscle. It is preferred that the injection be given in the fall preceding the influenza epidemic outbreak.

EXAMPLE 5

This example describes an influenza combination vaccine containing rHA0 and rNA.

The neuraminidase content of inactivated influenza vaccines is prone to variability, in part, because the concentration of inactivated virus in the final product is adjusted to produce the desired concentration of hemagglutinin. Although there is no minimum neuraminidase (NA) content required by the FDA for licensed vaccines in the United States, in Europe neuraminidase is required in licensed vaccines. The addition of a specified amount of recombinant NA to existing licensed vaccines or to the combination vaccine described in Example 1 or to the high dose combination vaccine described in Example 4 provides additional protection against disease from viral influenza.

Recombinant NA is produced using recombinant baculovirus expression vectors and lepidopteran cell cultures and extracted and purified under non-denaturing conditions to at least 90% purity (although NA of lesser or greater purity may also be used). The NA antigen is in the form of tetramers (although oligomeric forms or monomeric NA may also be used).

Combination inactivated virus/recombinant NA influenza vaccines are prepared from a standard adult dose of the commercially available influenza vaccines set out in Example 1 by addition of 0.5 ml recombinant NA trivalent antigens in phosphate buffered saline solution, pH 7. The NA trivalent antigens preparation contains the respective NA for each of the three influenza strains present in the commercial vaccine being used to make the combination vaccine. Each recombinant NA is adjusted to a final concentration of 10 μg per ml in the antigen preparation, so that following addition of the trivalent antigen to the inactivated virus vaccine the combination vaccine contains 5 μg of each recombinant NA.

Combination inactivated virus/recombinant HA0/recombinant NA influenza vaccines are prepared in accordance with the combination inactivated virus/recombinant HA0 vaccines described in Example 1 and the high dose combination vaccines described in Example 4 by addition of recombinant NA trivalent antigens in phosphate buffered saline solution, pH 7, to the HA0 trivalent antigens described in the Example. The resulting HA0/NA trivalent antigens preparation is added as described to the licensed inactivated vaccine. In the case of vaccines prepared in accordance with the combination vaccine described in Example 1, each NA is adjusted to a concentration of 10 μg per ml in the HA0/NA trivalent antigens preparation, so that, following addition of the trivalent antigens to the inactivated virus vaccine, the combination vaccine contains 5 μg of each recombinant NA and 15 μg of each recombinant HA0.

In the case of vaccines prepared in accordance with the combination vaccines described in Example 4, each NA is adjusted to a concentration of 100 μg per ml or to a concentration of 67 μg per ml, respectively, in the HA0/NA trivalent antigens preparation, so that, following addition of the trivalent antigens to the inactivated virus vaccine, the combination vaccine contains either 50 μg of each recombinant NA and 150 μg of each recombinant HA0 or 33.5 μg of each recombinant NA and 100 μg of each recombinant HA0. The NA trivalent antigens preparations contain the respective NA for each of the three influenza strains present in the commercial vaccine being used to make the combination vaccine.

The dosage of the combination vaccine is a single 1 ml dose administered by intramuscular injection in the deltoid muscle. It is preferred that the injection be given in the fall preceding the influenza epidemic outbreak.

The above description is intended to enable the person skilled in the art to practice the invention, and all references cited are expressly incorporated herein by reference. It is not intended to detail all of the possible modifications and variations which will become apparent to the skilled worker upon reading the description. It is intended, however, that all such modifications and variations be included within the scope of the invention which is defined by the following claims. The claims are meant to cover the indicated elements and steps in any arrangement or sequence which is effective to meet the objectives intended for the invention, unless the context specifically indicates the contrary.

I claim:

1. In a vaccine composition which comprises an antiinfluenza vaccine, wherein the improvement comprises having as an additive:

substantially pure, recombinant influenza neuraminidase protein produced by a baculovirus expression system in cultured insect cells, wherein said protein is purified to 90% or greater.

2. In a vaccine composition which comprises an antiinfluenza vaccine, wherein the improvement comprises having as an additive:

a combination of:

substantially pure, recombinant, mature, glycosylated influenza hemagglutinin protein produced by a baculovirus expression system in cultured insect cells, wherein said protein is purified to 90% or greater and said protein is immunogenic, and induces a protective immune response when used as a vaccine; and, substantially pure, recombinant influenza neuraminidase protein produced by a baculovirus expression system in cultured insect cells, wherein said protein is purified to 90% or greater.

3. The vaccine composition of claim 2 wherein the hemagglutinin protein is the HA0 subunit.

4. The vaccine composition of any one of claims 1 to wherein the anti-influenza vaccine comprises three inactivated strains of influenza virus.

5. The vaccine composition of any one of claims 1 to which includes an adjuvant.

6. The vaccine composition of claim 4 which includes an adjuvant.

7. A method for vaccinating a mammal against influenza comprising administering to the mammal an effective amount of the vaccine composition of any one of claims 1 to 3.

8. A method for vaccinating a mammal against influenza comprising administering to the mammal an effective amount of the vaccine composition of claim 4.

9. A method for vaccinating a mammal against influenza comprising administering to the mammal an effective amount of the vaccine composition of claim 5.

10. A method for vaccinating a mammal against influenza comprising administering to the mammal an effective amount of the vaccine composition of claim 6.

11. The method of claim 7 wherein the mammal is a human.

* * * * *

UNITED STATES PATENT AND TRADEMARK OFFICE
CERTIFICATE OF CORRECTION

PATENT NO. : 5,976,552
DATED : November 02, 1999
INVENTOR(S) : GALE EUGENE, BETHANIE E. WILKINSON, ANDREI I. VOZNESENSKY, CRAIG S. HACKETT, AND FRANKLIN VOLVOVITZ It is certified that error appears in the above-identified patent and that said Letters Patent is hereby corrected as shown below:

On the title page, item [75] Inventors:
Please add --GALE EUGENE SMITH, WALLINGFORD, CT; BETHANIE E. WILKINSON, HIGGANUM, CT; ANDREI I. VOZNESENSKY, WEST HARTFORD, CT; AND CRAIG S HACKETT, WALLINGFORD, CT-- as inventors on the above-captioned patent and the order of the named inventors should read as follows: GALE EUGENE SMITH, WALLINGFORD, CT; BETHANIE E. WILKINSON, HIGGANUM, CT; ANDREI I. VOZNESENSKY, WEST HARTFORD, CT; CRAIG S. HACKETT, WALLINGFORD, CT; AND FRANKLIN VOLVOVITZ, WOODBRIDGE, CT.-- item (*):
Please delete the asterick (*) and the Notice that the patent is subject to a terminal disclaimer (as it is not).

Signed and Sealed this

Twenty-eighth Day of November, 2000

Attest:

Q. TODD DICKINSON

Attesting Officer

Director of Patents and Trademarks